US00PP28571P2

(12) United States Plant Patent
Korlipara

(10) Patent No.: US PP28,571 P2
(45) Date of Patent: Oct. 24, 2017

(54) ***COREOPSIS* PLANT NAMED 'TNCORHRG'**

(50) Latin Name: ***Coreopsis verticillata* hybrid**
Varietal Denomination: TNCORHRG

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 15/330,200

(22) Filed: Aug. 22, 2016

(51) Int. Cl.
*A01H 5/02* (2006.01)

(52) U.S. Cl.
USPC ..... Plt./417

(58) Field of Classification Search
USPC ..... Plt./417
See application file for complete search history.

*Primary Examiner* — Annette H Para
(74) *Attorney, Agent, or Firm* — Klarquist Sparkman, LLP

(57) ABSTRACT

A new and distinct *Coreopsis* plant named 'TNCORHRG' characterized by small, daisy-type inflorescences, inflorescences that are gold with large dark red eyes, hardy to Zone 6, maybe lower, grass green foliage on short stems, flowering for the whole summer, a tight, compact, rounded, mounding habit, and excellent vigor.

1 Drawing Sheet

Latin name: *Coreopsis verticillata* hybrid.
Varietal denomination: 'TNCORHRG'.

BACKGROUND OF THE INVENTION

The present invention relates to a new and distinct *Coreopsis* and given the cultivar name 'TNCORHRG'. *Coreopsis* is in the family Asteraceae. This new cultivar originated from a controlled breeding program to produce hardy compact *Coreopsis*. The new cultivar originated from planned cross of two proprietary unnamed *Coreopsis verticillata* hybrid seedlings. The new cultivar of *Coreopsis* is an herbaceous perennial to be grown for landscape and container use in a sunny site.

Compared to *Coreopsis* 'Firefly', U.S. Plant Pat. No. 26,295, the new cultivar has a rounder, tighter habit and has ray florets that are gold rather than dark yellow and with larger dark red eyes.

Compared to *Coreopsis* 'Curry Up' unpatented, the new cultivar is smaller and more compact overall.

SUMMARY OF THE INVENTION

The following traits have been repeatedly observed and are determined to be the unique characteristics of the new variety. These characteristics in combination distinguish *Coreopsis* 'TNCORHRG' as a new and distinct cultivar:

1. small daisy-type inflorescences,
2. inflorescences that are gold with large dark red eyes,
3. hardy to Zone 6, maybe lower,
4. grass green foliage on short stems,
5. flowering for the whole summer,
6. a tight, compact, rounded, mounding habit, and
7. excellent vigor.

This new cultivar has been reproduced only by asexual propagation (cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a nine-month-old *Coreopsis* 'TNCORHRG' growing in the ground in the trial field in July in Canby, Oreg.

FIG. 2 shows a close up of the flowers.

DETAILED PLANT DESCRIPTION

The following is a detailed description of the new *Coreopsis* cultivar based on observations of nine-month-old specimens growing in one gallon containers outside in full sun in September in Canby, Oreg. Canby is Zone 8 on the USDA Hardiness map. Temperatures range from a high of 95° F. in August to 32° F. in January. Normal rainfall in Canby is 42.8 inches per year. The color descriptions are all based on *The Royal Horticultural Society Colour Chart*, 5$^{th}$ edition, 2007.

Plant:

*Type*.—Herbaceous perennial.
*Hardiness*.—USDA Zones 6 to 9.
*Size*.—35 cm wide and 23 cm tall to top of inflorescences.
*Form*.—Tight mound.
*Vigor*.—Excellent.
*Roots*.—Fibrous, stems root easily from stem cuttings.

Stem:

*Type*.—Ascending, well branched.
*Size*.—Grows to 22 cm tall and 3 mm wide.
*Number of stems from the crown*.—25.

*Branching habit*.—Freely branched, an average of 7 paired lateral branches with secondary branches, branches are opposite in arrangement, new lateral flowering branches are continuously produced throughout the summer.

*Internode length*.—1 cm to 3.5 cm.

*Surface*.—Glabrous.

*Color*.—Brown 200B at bottom 5 cm blending to Yellow Green 147B.

Leaf:

*Type*.—Simple.

*Shape*.—Pinnately 3 to 5 parted with thread-like segments, to linear on top leaves.

*Arrangement*.—Opposite.

*Size*.—Thread-like segments can spread to 8 cm wide and 6 cm long, the linear segments can grow to 43 mm long and 3.5 mm wide.

*Apex*.—Acute.

*Margins*.—Entire.

*Petiole*.—0 mm to 9 mm long and 1.5 mm wide, Green 137B.

*Surface texture*.—Glabrous on top and sparsely pubescent on bottom side.

*Venation*.—Pinnate, visible main vein the same color as the leaf on both sides.

*Color*.—Topside Yellow Green 147A, bottom side Yellow Green 147B.

Inflorescence:

*Type*.—Long stalked terminal heads of daisy type inflorescences.

*Peduncle*.—Grows to 3.5 cm long, 1 mm wide, glabrous, Yellow Green 147A.

*Size*.—Grows to 3.3 cm wide and 10 mm deep.

*Immature* (*bud*).—Globular, 3 mm wide and 5 mm deep, Yellow Green 147B, glabrous.

*Receptacle*.—Disc shaped, 3 mm wide and 1.5 mm deep, Green 148B.

*Phyllaries*.—In 2 series; first series closet to ray florets in an area 6 mm deep and spreading 7 mm wide, 8 in number, each 6 mm long and 2 mm wide, lanceolate, margin entire, tip acute, glabrous on both sides, both sides Yellow Green 147B; lower series in an area 3 mm deep and 11 mm wide, 8 linear lobes, each about 5 mm long and 1 mm wide, margin entire, tip acute, top side glandular, bottom side glabrous, both sides Yellow Green 147A.

*Self-cleaning*.—Yes.

*Lastingness*.—Each inflorescence lasts about a week on the plant.

Florets:

*Type*.—Composite.

*Ray florets*.—8 in number with no pistil or stamen, grows to 18 mm long, 6.5 mm wide, obovate, with the tip obtuse to 2 notched, margins entire, glabrous on both sides; topside Yellow 9A on top half, Greyed Purple 187B on bottom half, bottom side Yellow 7C on top half to Grey Brown N199D on bottom half.

*Disc*.—Flat becoming rounded with maturity, 6 mm wide and becoming 4 mm deep with maturity, Greyed Purple 187A.

*Disc florets*.—Tubular, with stamen and pistil, about 40 in number, 6 mm long and 1 mm wide, tubular; corolla 5 mm long, 5 lobed, tube Yellow 9A, lobes Greyed Purple 187A; pistil 1, 4 mm long, ovary 2 mm long, Green Yellow 1C, style 4 mm long, with extruding, 2-branched stigma, stigma and style Yellow Orange 22A; stamen 5, anthers 1 mm long, Greyed Brown N199B, pollen none.

*Bloom period*.—June through frost in Canby, Oreg.

*Fragrance*.—No noticeable.

*Seed*.—None seen.

*Fertility*.—Unknown.

Disease and pests: No pests or diseases have been observed on plants grown under commercial conditions in Canby, Oreg. No resistances are known.

I claim:

1. A new and distinct *Coreopsis* plant as herein illustrated and described.

* * * * *

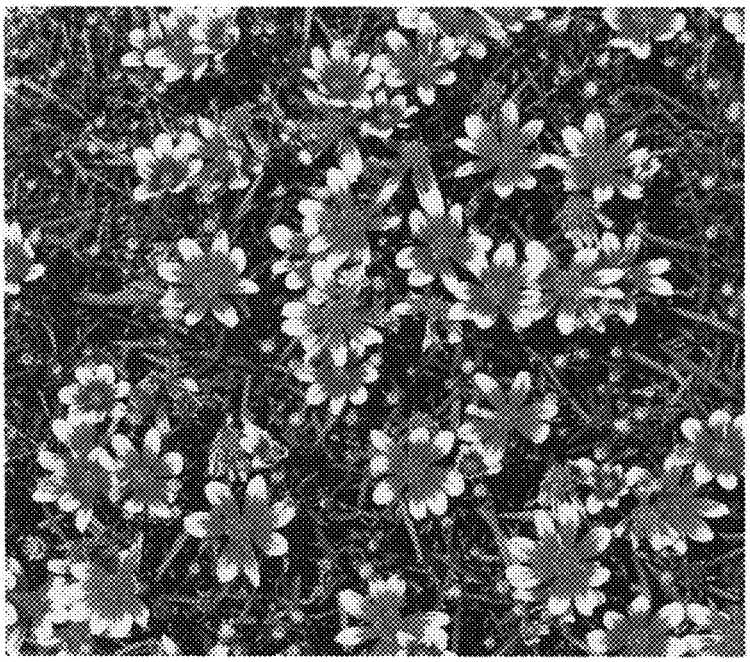

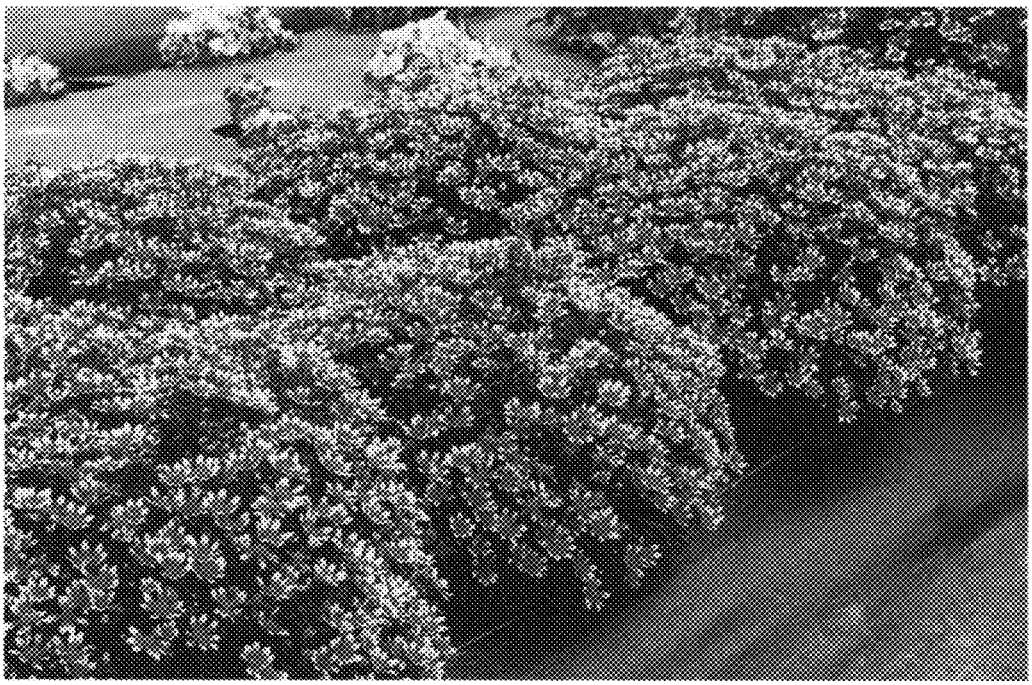
FIG. 1 above, FIG. 2 below